US007842720B2

(12) United States Patent
Elsohly et al.

(10) Patent No.: US 7,842,720 B2
(45) Date of Patent: Nov. 30, 2010

(54) ANTICANCER AND ANTIPROTOZOAL DIHYDROARTEMISINENE AND DIHYDROARTEMISITENE DIMERS WITH DESIRABLE CHEMICAL FUNCTIONALITIES

(75) Inventors: Mahmoud A. Elsohly, Oxford, MS (US); Waseem Gul, Oxford, MS (US)

(73) Assignee: Elsohly Laboratories, Incorporated, Oxford, MS (US)

( * ) Notice: Subject to any disclaimer, the term of this patent is extended or adjusted under 35 U.S.C. 154(b) by 885 days.

(21) Appl. No.: 11/570,652

(22) PCT Filed: Jun. 21, 2005

(86) PCT No.: PCT/US2005/021826

§ 371 (c)(1),
(2), (4) Date: Feb. 13, 2007

(87) PCT Pub. No.: WO2006/002105

PCT Pub. Date: Jan. 5, 2006

(65) Prior Publication Data

US 2008/0275106 A1    Nov. 6, 2008

Related U.S. Application Data

(60) Provisional application No. 60/581,412, filed on Jun. 21, 2004.

(51) Int. Cl.
*A61K 31/357*   (2006.01)
*C07D 323/00*   (2006.01)
(52) U.S. Cl. ..................................... 514/450; 549/348
(58) Field of Classification Search ................. 549/348; 514/450
See application file for complete search history.

(56) References Cited

U.S. PATENT DOCUMENTS

| 5,677,468 | A | 10/1997 | Zheng et al. |
| 5,840,925 | A | 11/1998 | Zheng et al. |
| 5,856,351 | A | 1/1999 | Zheng et al. |
| 6,790,863 | B2 * | 9/2004 | ElSohly et al. ............... 514/450 |
| 2004/0072896 | A1 * | 4/2004 | ElSohly et al. ............... 514/452 |
| 2004/0229938 | A1 | 11/2004 | ElSohly |
| 2004/0266860 | A1 | 12/2004 | ElSohly |

FOREIGN PATENT DOCUMENTS

| WO | WO 97/01548 | 1/1997 |
| WO | WO 99/65914 | 12/1999 |
| WO | WO 03/035651 A2 | 1/2003 |
| WO | WO 2004/028476 A2 | 4/2004 |

OTHER PUBLICATIONS

Posner, G. et al., "Malaria-Infected Mice are cured by a single dose of Novel Artemisinin Derivatives" J. Med. Chem., 50:2516-2519 (2007).

Paik, Ik-Hycon et al., "Second Generation, Orally Active, Antimalarial, Artemisinin-Derived Trioxane Dimers with High Stability, Efficacy, and Anticancer Activity" J. Med. Chem., 49:2731-2734 (2006).

Grellepois, F. et al., "Synthesis of New Artemisinin-Derived Dimers by Self-Cross-Metathesis Reaction" Organic Letters, 7(23):5219-5222 (2005).

Jung, M. et al., "Recent Advances in Artemisinin and Its Derivatives as Antimalarial and Antitumor Agents" Current Medicinal Chemistry, 11:1265-1284 (2004).

Posner, G. et al., "Anticancer and Antimalarial Efficacy and Safety of Artemisinin-Dervied Trioxane Dimers in Rodents" J. Med. Chem., 47:1299-1301 (2004).

Posner, G. et al., "Orally Active, Antimalarial, Anticancer, Artemisinin-Derived Trioxane Dimers with High Stability and Efficacy" J. Med. Chem., 46:1060-1065 (2003).

Posner, G. et al., "New Chemical and Biological Aspects of Artemisinin-Derived Trioxane Dimers" Bioorganic & Medicinal Chemistry, 10:227-232 (2002).

Ekthawatchai, S. et al., "C-16 Artemisinin Derivatives and Their Antimalarial and Cytotoxic Activities: Syntheses of Artemisinin Monomers, Dimers, Trimers, and Tetramers by Nucleophilic Additions to Artemisitene" J. Med. Chem., 44:4688-4695 (2001).

Robert, A. et al., "Characterization of the Alkylation Product of Heme by the Antimalarial Drug Artemisinin" Angew. Chem. Int. Ed. 40(10) 1954-1957 (2001).

Kapetanaki, S. et al., "Ferryl-oxo heme intermediate in the antimalarial mode of action of artemisinin" Federation of European Biochemical Societies, Letters 474: 238-241 (2000).

Usuda, M. et al., "Interaction of Antimalarial Agent Artemisinin with Cyclodextrins" Drug Development and Industrial Pharmacy, 26(6):613-619 (2000).

Li, Ying. et al., "Synthesis and Antimalarial Activity of Artemisinin Derivatives Containing and Amino Group" J. Med. Chem. 43:1635-1640 (2000).

Posner, G. et al., "Antimalarial, antiproliferatie, and Antitumor Activities of Artemisinin-Derived, Chemically Robust, Tioxane Dimers" J. of Medicinal Chem. 42(21): 4275-4280 (1999).

Posner, G. et al., "Trioxane Dimers have Potent Antimalarial, Antiproliferative and Antitumor Activities In Vitro" Bioorganic & Medicinal Chemistry, 5(7): 1257-1265 (1997).

Galal, A. et al., "Preparation and characterization of a New Artemisinin-Derived Dimer" J. Nat. Prod. 59:917-920 (1996).

(Continued)

*Primary Examiner*—Bernard Dentz
(74) *Attorney, Agent, or Firm*—Hershkovitz & Associates LLC; Abraham Hershkovitz; Eugene C. Rzucidlo

(57) ABSTRACT

This invention comprises compositions containing dihydroartemisinin- and dihydroartemisitene-dimers with activity as anticancer or anticancer metastasis agents and antiprotzal, including anti-malarial and anti-leishmanial properties. This invention also describes methods of preparation of these compositions and methods of use of such compositions for the treatment of cancer or prevention of cancer metastasis, and protozoal infections, including malaria, or leishmaniasis. The compounds of this invention represent a potential new class of anti-tumor or anti-metastasis agents, one that has shown promising activity against solid tumors.

49 Claims, 6 Drawing Sheets

OTHER PUBLICATIONS

Beekman, A. et al., "Cytotoxicity of Artemisinin, a Dimer of Dihyroartemisinin, Artemisitene and Eupatoriopicrin as Evaluated by the MTT and Clonogenic Assay" Phytotherapy Research, 10:140-144 (1996).

Meshnick, S. et al., "Iron-Dependent Free Radical Generation from the Antimalarial Agent Artemisinin (Qinghaosu)" Antimicrobial Agents and Chemotherapy, 37(5): 1108-1114 (1993).

Jung, M. et al. "Recent advances in artemisinin and its derivatives as antimalarial and antitumor agents" Current Medicinal Chemistry 200405 NL, vol. 11, No. 10, May 2004.

Posner et al. Trioxane dimers have potent antimalarial, antiproliferative and antitumor activites in vitro: Bioorganic & Medicinal Chemistry, Pergamon, GB, vol. 7, No. 7, Jan. 1997.

Supplemental European Search Report corresponding to EP 05 76 2351 issued Feb. 11, 2010.

* cited by examiner

Compound (1)

Compound (2)

Compound (3)

Compound (5)

Compound (4)

Compound (6)

Compound (7)

Compound (8)

Compound (9)

Compound (10)

Compound (11)

Compound (12)

Compound (13)

Figure 2

Anticancer activity against SK-MEL, KB, BT-549 and SK-OV3 cells (values are IC$_{50}$ in µg/ml) and Cytotoxicity to Vero and PK-1 cells

| Compound # | SK-MEL | KB | BT-549 | SK-OV-3 | VERO | PK-1 |
|---|---|---|---|---|---|---|
| 6 | 0.1 | 0.1 | 0.55 | NA | 0.50 | 0.7 |
| 7 | 0.30 | 0.085 | 0.9 | 0.87 | 0.50 | 0.08 |
| 9 | 0.06 | 0.035 | 0.9 | >10 | 0.32 | 0.15 |
| Doxorubicin | <1.1 | <1.1 | <1.1 | 1.8 | 5.8 | <1.1 |
| 8 | 0.27 | 0.034 | 0.17 | NA | NC | 0.80 |
| Doxorubicin | 0.55 | <0.55 | <0.55 | 0.8 | >5.0 | 0.75 |
| 10 | >10 | 4.50 | 4.50 | NA | NA | >10 |
| 11 | 10.0 | 0.37 | 9.50 | NA | 10.0 | 6.0 |
| Doxorubicin | 0.90 | 0.16 | 0.25 | 1.70 | >5.0 | 0.25 |
| Paclitaxel | 3.50 | 0.017 | 0.02 | 0.45 | 0.45 | 3.75 |
| 4 | 0.35 | 0.15 | 0.15 | NA | >5 | 0.065 |
| Glutarate of 5 | >5 | 2.1 | 2.7 | NA | 5 | 0.075 |
| Succinate of 5 | >5 | 1.7 | 0.64 | NA | 4 | 0.048 |
| 5 | 5 | 0.16 | 0.3 | NA | 3.5 | 0.091 |
| Doxorubicin | 0.5 | <0.55 | <0.55 | 1.2 | 5 | <0.55 |
| 12 | 0.37 | 0.25 | 0.36 | NA | <0.1 | |
| 13 | 5.0 | 7.2 | NA | NA | 4.5 | |
| Doxorubicin | 0.17 | 0.16 | 0.18 | 0.15 | 0.9 | | highest test conc. = 10 µg/ml for compounds; 5µg/ml for Doxorubicin; and 4.25 µg/ml for Paclitaxel
NA and NC not active and not cytotoxic up to 10 µg/ml

| Cell line | Description |
|---|---|
| SK-MEL | human malignant, melanoma |
| KB | human epidermal carcinoma, oral |
| BT549 | ductal carcinoma, breast |
| SK-OV3 | human ovary carcinoma |
| VERO | monkey kidney fibroblast |
| LLC-PK1 | Pig Kidney epithelial |

Figure 3

Antimalarial Activity of Compounds 6-11

| Compound # | P. falciparum (D6 Clone) | | P. falciparum (W2 Clone) | | Cytotoxicity (Vero Cells) |
|---|---|---|---|---|---|
| | $IC_{50}$ ng/ml | S.I. | $IC_{50}$ ng/ml | S.I. | $IC_{50}$ ng/ml |
| 6* | 18 | 8.9 | 15 | 10.7 | 160 |
| Artimisinin | 14.5 | | 7.0 | | |
| Chloroquine | 17.0 | | 70 | | |
| 7*** | 80 | 3.8 | 29 | 10.3 | 300 |
| Artimisinin | 14.0 | | 14.0 | | |
| Chloroquine | 15.0 | | 125.0 | | |
| 8*** | 56 | >85 | 43 | >110.7 | NC |
| 9*** | 12 | 33.3 | 5 | 87 | 400 |
| Artimisinin | 13.5 | | 6.0 | | |
| Chloroquine | 12.5 | | 140 | | |
| 10** | 120 | >39.7 | 97 | >49.1 | NC |
| Artimisinin | 5.5 | | 8.5 | | |
| Chloroquine | 7.0 | | 90 | | |
| 11*** | 13 | >366.2 | 8.3 | >573.5 | NC |
| Artimisinin | 12.0 | | 6.5 | | |
| Chloroquine | 16.5 | | 120 | | |

\* tested at 3 concentrations: 238, 79.3 and 26.4 ng/ml
\*\* tested at 6 concentrations: 4760, 1587, 529, 176, 56, 19.5 ng/ml
\*\*\* tested at 6 concentrations: 476, 159, 53, 18, 6, 1.95 ng/ml
Selectivity Index (S.I.) = $IC_{50}$ (Vero Cells) / $IC_{50}$ (P. falciparum)
NA = Inactive, NC = No Cytotoxicity

Figure 4

Anti-Leishmanial Activity of Compounds 6-13

| Compound | $IC_{50}$ | $IC_{90}$ |
|---|---|---|
| 6* | 15 | 35 |
| Pentamidine | 1.8 | 8.5 |
| Amphotericine B | 0.17 | 1.7 |
| 7* | 2.5 | 7 |
| Pentamidine | 1.6 | 8.0 |
| Amphotericine B | 0.17 | 0.34 |
| 8* | 12 | >40 |
| Pentamidine | 1.6 | 6.6 |
| Amphotericine B | 0.17 | 0.34 |
| 9** | 4.6 | 26 |
| Pentamidine | 1.5 | 4.5 |
| Amphotericine B | 0.28 | 0.78 |
| 10* | <1.6 | 3.7 |
| Pentamidine | 1.3 | 6 |
| Amphotericine B | 0.18 | 0.35 |
| 11** | 13 | >40 |
| Pentamidine | 2.2 | 6.2 |
| Amphotericine B | NA | NA |
| 12* | 5.5 | 36 |
| 13* | 18 | 38 |
| Pentamidine | 1.0 | 4.5 |
| Amphotericine B | 0.17 | 0.34 |

*Tested at 3 concentration: 40, 8, 1.6 µg/mL
**Tested at 6 concentration: 40, 8, 1.6, 0.32, 0.064, 0.0128 µg/mL
$IC_{50}$ and $IC_{90}$ are the sample concentrations that kill 50% and 90% cells compared to the solvent controls.
NA = Not active

ANTICANCER AND ANTIPROTOZOAL DIHYDROARTEMISINENE AND DIHYDROARTEMISITENE DIMERS WITH DESIRABLE CHEMICAL FUNCTIONALITIES

FIELD OF INVENTION

The present invention relates to dihydroartemisinin and dihydroartemisitene dimers and their use in the treatment of cancer and as antiprotzoal agents.

BACKGROUND OF THE INVENTION

Cancer deaths in the U.S. alone were over 500,000 in 2001, and in spite of many advances, cancer remains one of the leading killers (1). There is a critical need for the development of new anti-cancer agents, especially those with novel and selective mechanisms of action. Although some of the promise of non-cytotoxic therapies is beginning to be realized (e.g. immunostimulants, growth factor antagonists, anti-sense therapy), the mainstay of the treatment of most cancers remains with cytotoxic drugs. In view of the limited success rates, incidence of toxicities, and development of resistance to such agents, there is a dire need for new classes of these drugs, especially those that may act by new mechanisms or exhibit exploitable selectivity. There is also a need for a better understanding of dosing, scheduling, and concomitant therapies in order to optimize treatment protocols.

Natural products have historically been a rich source of new, successful prototype classes of lead compounds from which analogs have been developed. According to a recent review, 60% of the anti-infective and anti-cancer drugs that have successfully advanced to the clinic are derived from natural products (2). Examples of these among currently used anti-cancer agents include the anthracycline class (e.g., doxorubicin), the Catharanthus (Vinca) alkaloids, paclitaxel, and derivatives of podophyllotoxin and camptothecin. A recently published tabulation of natural product-based anti-tumor drugs shows more than 25 agents currently in Phase I or II (3). This and other recent reviews are important reminders of the critical role of natural products as a resource for the discovery of new anti-tumor agents (4,5).

The natural product artemisinin (1) is a sesquiterpene endoperoxide first isolated in 1971 from the Chinese plant *Artemisia annua* (6). The compounds as numbered herein are depicted in FIG. 1. The compound was shown to have antimalarial activity against both chloroquine-sensitive and chloroquine-resistant strains of *Plasmodium falciparum*.

Because of the importance of the clinical effects of artemisinin in treating malaria, many derivatives were prepared in order to develop the most effective and least toxic anti-malarial agent. Initially, simple derivatives were prepared—e.g., dihydroartemisinin (DHA, in which the lactone carbonyl is reduced resulting in a hemiacetal), artemether (the methyl ether of DHA) and several other ether and ester analogs. The sodium salt of the hemisuccinate ester (sodium artesunate) was one of these derivatives that showed more activity and less toxicity than artemether, the latter being more active than artemisinin itself. Continued interest in the activity of artemisinin and DHA analogs later resulted in the preparation of artemisinin acetal dimers through reaction of dihydroartemisinin with borontrifluoride-etherate.

In addition to its anti-malarial activity, artemisinin had been reported to have cytotoxic effects against EN-2 tumor cells (7), P-388, A549, HT-29, MCF-7, and KB-tumor cells (8). As more analogs were evaluated for anti-tumor activity, it was reported that the unsymmetrical dimer (2) showed strong cytotoxic activity and was more potent than cisplatin (9). The symmetrical dimer (3) also showed pronounced cytotoxic activity (10).

This finding stimulated interest in other types of DHA dimers. Posner et al. (11) prepared dimers linked with a polyethylene glycol spacer (3 units of ethylene glycol), an eight carbon glycol, and a dithio-derivative. The authors also prepared simpler trioxane dimers. Posner et al. also prepared several dimers of DHA where the linking units between the two molecules of dihydroartemisinin were dicarboxylic acids of different types (12). Zhang and Darbie (13,14) also proposed several dihydroartemisinin dimers to be linked via different coupling agents. Some of these artemisinin dimers and some of the simpler trioxanes had anti-malarial effects, anti-cancer activity, and anti-proliferative effects with some compounds being as active as calcitriol in an anti-proliferative assay in murine keratinocytes.

More recently, ElSohly et al (15) prepared a series of DHA dimers with 1,2- and 1,3-glycols which were active in the anticancer screen carried out at the National Cancer Institute (NCI). The compounds showed promising selectivity in the 60-cell line anticancer screen, as well as activity in the anti-malarial and anti-leishmanial screens. While these dimers have good activity in the anticancer and anti-protozoal screens, they have limited water solubility which impose difficulties in formulation.

SUMMARY OF THE INVENTION

This invention comprises compositions containing dihydroartemisinin and dihydroartemisitene dimers with activity as anticancer agents and anti-protozoal, including anti-malarial and anti-leishmanial properties. This invention also describes methods of preparation of these compositions and methods of use of such compositions for the treatment of cancer, and protozoal infections, including malaria, or leishmaniasis. The compositions of this invention have not been previously described.

The compounds of this invention represent a potential new class of anti-tumor agents, one that has shown promising activity and with chemical functionalities that will improve formulation characteristics.

DESCRIPTION OF THE INVENTION

In the interest of development of new chemotherapeutic agents, artemisinin dimers were prepared in this invention by condensation of DHA with dihydroxy acetone to generate the dimer depicted in structure 4 which is used as the starting material for all dimers based on DHA and the corresponding analogs based on dihydroartemisitene.

The present invention relates to compounds of the formula:

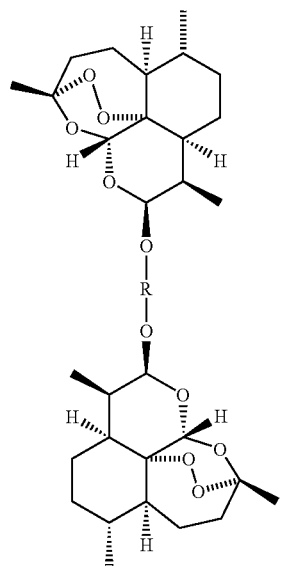

where R is

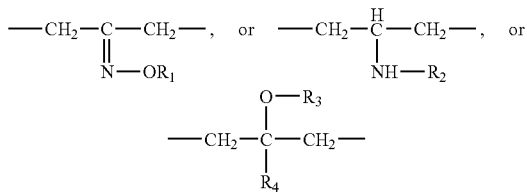

where $R_1$ is H or alkyl, cycloalkyl or aryl moiety, free or containing one of a variety of functional groups such as COOH, OH, NH or derivatives thereof;

where $R_2$ is H or alkyl, cycloalkyl or aryl moiety, free or containing one of a variety of functional groups such as COOH, OH, $NH_2$ or derivatives thereof;

where $R_3$ is an alkyl, cycloalkyl or aryl residue with acidic functional group (such as COOH), a sulfate ($SO_3H$), a phosphate ($PO_3H_2$) ester or basic functionality (such as primary, secondary or tertiary amine) and $R_4$ is H; OR where $R_3$ is H and $R_4$ is an alkyl, cycloalkyl or aryl residue with acidic or basic functionality; OR where $R_4$ is H and $R_3$ is an ester or carbamate residue, such residue might be containing other functional groups such as COOH, OH, amino, or sugar moiety;

or compounds of the formula

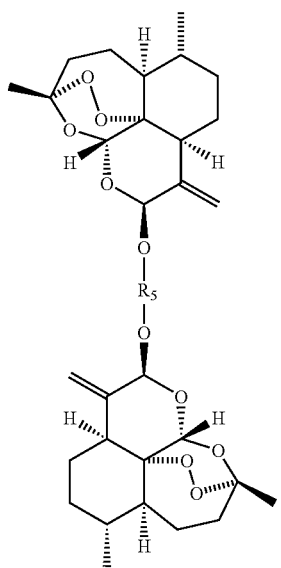

where $R_5$ is selected from one of the substituents described above for R.

Furthermore, the present invention includes pharmaceutical compositions comprising at least one of the compounds according to the above formulas and pharmaceutically acceptable carrier and/or excipient.

The compounds of the invention can be prepared by reacting dihydroartemisin or dihydroartemistene with dihydroxy acetone under acidic conditions such as borontrifluoride etherate followed by additional functionalization of the resulting ketone dimer.

Compounds where R is

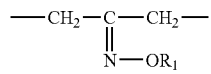

residue and $R_1$ is selected from H, or alkyl, cycloalkyl or aryl groups free or containing one of a variety of functional groups such as COOH, OH or $NH_2$ or derivatives thereof are prepared by reacting the ketone dimer from the reaction product of DHA with dihyrdroxy acetone with $NH_2$—O—$R_1$ (where $R_1$ is the appropriate substituent) under basic conditions followed by purification of the reaction mixture to separate the purified oxime.

Compounds where R is

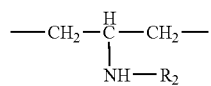

residue and $R_2$ is selected from H, or alkyl, cycloalkyl or aryl groups free or containing one of a variety of functional groups such as COOH, OH or $NH_2$ or derivatives thereof are prepared by reacting the ketone dimer from dihydroxy acetone with $NH_2$—$R_2$ (where $R_2$ is the appropriate substituent) and sodium cyanoborohydride or sodium triacetoxyborohydride, followed by purification of the reaction mixture to separate the purified amine. Alternatively, compounds where R is

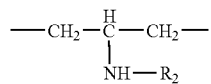

could be directly prepared by reacting DHA with the 1,3-diol containing the appropriate substituent at the 2 position, in the presence of an acid catalyst such as borontrifluoride etherate.

Compounds where R is

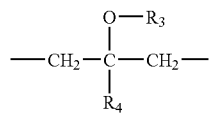

residue and where $R_3$ is an alkyl, cycloalkyl or aryl residue with acidic functional group (such as COOH), a sulfate ($SO_3H$), a phosphate ($PO_3H_2$) ester, or basic functionality (such as primary, secondary or tertiary amine) and $R_4$ is H; OR where $R_3$ is H and $R_4$ is an alkyl, cycloalkyl or aryl residue with acidic or basic functionality; OR where $R_4$ is H and $R_3$ is an ester or carbamate residue, such residue might be containing functional groups such as COOH, OH, amino, or sugar moiety, are prepared by reacting the ketone dimer from dihydroxy acetone with the proper nucleophile or by first reducing the ketone dimer with sodium borohydride followed by reacting the resulting alcohol with the proper reagent to produce the desired product.

Compounds where $R_5$ is

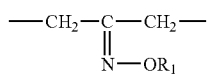

residue and $R_1$ is selected from H, or alkyl, cycloalkyl or aryl groups free or containing one of a variety of functional groups such as COOH, OH or NH or derivatives thereof are prepared by reacting the ketone dimer of dihydroxy acetone and dihydroartemisitene with $NH_2$—O—$R_1$ (where $R_1$ is the appropriate substituent) under basic conditions followed by purification of the reaction mixture to separate the purified oxime.

Compounds where $R_5$ is

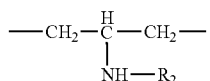

residue and $R_2$ is selected from H, or alkyl, cycloalkyl or aryl groups free or containing one of a variety of functional groups such as COOH, OH or $NH_2$ or derivatives thereof are prepared by reacting the ketone dimer from dihydroxy acetone and dihydroartemisitene with $NH_2$—$R_2$ (where $R_2$ is the appropriate substituent) and sodium cyanoborohydride or sodium triacetoxyborohydride, followed by purification of the reaction mixture to separate the purified amine.

Compounds where $R_5$ is

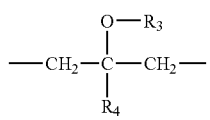

residue and where $R_3$ is an alkyl, cycloalkyl or aryl residue with acidic functional group such as COOH, a sulfate ($SO_3H$), a phosphate ($PO_3H_2$) ester, or basic functionality (such as primary, secondary or tertiary amine) and $R_4$ is H; OR where $R_3$ is H and $R_4$ is an alkyl, cycloalkyl or aryl residue with acidic or basic functionality; OR where $R_4$ is H and $R_3$ is an ester or carbamate residue, such residue might be containing functional groups such as COOH, OH, amino, or sugar moiety are prepared by reacting the ketone dimer from dihydroxy acetone and dihydroartemisitene with the proper nucleophile or by first reducing the ketone dimer with sodium borohydride followed by reacting the resulting alcohol with the proper reagent to produce the desired product.

As used herein, the term "alkyl" refers to a straight or branched chain hydrocarbon having from one to ten carbon atoms, optionally substituted with appropriate substituents. Examples of "alkyl" as used herein include, but are not limited to, methyl, ethyl, propyl, n-butyl, t-butyl, n-pentyl, isobutyl, and isopropyl, and the like.

As used herein, "cycloalkyl" refers to an alicyclic hydrocarbon group optionally possessing one or more degrees of unsaturation, having from three to six carbon atoms, optionally substituted with appropriate substituents.

"Cycloalkyl" includes by way of example cyclopropyl, cyclobutyl, cyclopentyl, or cyclohexyl, and the like.

As used herein, the term "aryl" refers to a benzene ring, optionally substituted with appropriate substituents. Examples of aryl include, but are not limited to, phenyl.

The invention further comprises a method of treating cancer, prevention or control of cancer metastasis or treating protozoal infections, comprising administering to a subject suffering from cancer or a protozoal infection an effective amount of at least one compound of one of the formulae:

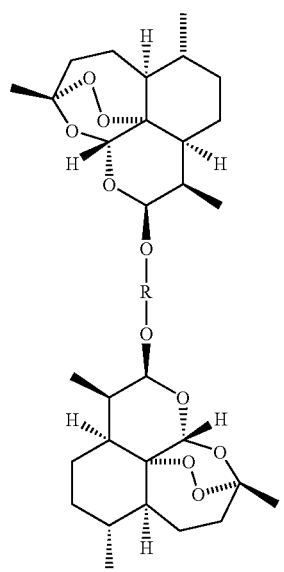

where R is

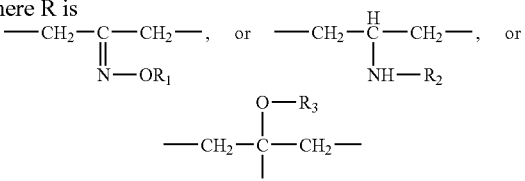

where $R_1$ is H or alkyl, cycloalkyl or aryl moiety, free or containing one of a variety of functional groups such as COOH, OH, NH or derivatives thereof;

where $R_2$ is H or alkyl, cycloalkyl or aryl moiety, free or containing one of a variety of functional groups such as COOH, OH, NH or derivatives thereof;

where $R_3$ is an alkyl, cycloalkyl or aryl residue with acidic functional group such as COOH, a sulfate ($SO_3H$), a phosphate ($PO_3H_2$) ester or basic functionality (such as primary, secondary or tertiary amine) and $R_4$ is H; OR where $R_3$ is H and $R_4$ is an alkyl, cycloalkyl or aryl residue with acidic or basic functionality; OR where $R_4$ is H and $R_3$ is an ester or carbamate residue, such residue might be containing functional groups such as COOH, OH, amino, or sugar moiety;

or a compound of the formula:

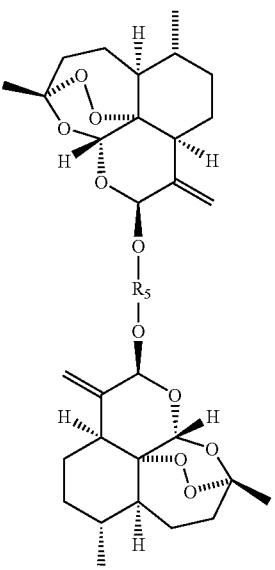

where $R_5$ is selected from one of the substituents described above for R.

Administration of the instant dimers may be by any of the conventional routes of administration, for example, oral, subcutaneous, intraperitoneal, intramuscular, intravenous or rectally. In the preferred embodiment, the compound is administered in combination with a pharmaceutically-acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include saline, water, buffer solutions, edible oils, e.g. peanut and corn oils.

When administered in solid form, the compound and diluent carrier may be in the form of tablets, capsules, powders, or suppositories, prepared by any of the well known methods. When given as a liquid preparation, the mixture of active compound and liquid diluent carrier may be in the form of a suspension administered as such, an emulsion, or a true solution. The compound is administered in a non-toxic dosage concentration sufficient to inhibit the growth and/or destroy cancer or prevent cancer metastasis or to destroy protozoal organisms such as malaria and *leishmania*. The actual dosage unit will be determined by the well recognized factors as body weight of the patient and/or severity and type of pathological condition the patient might be suffering with. With these considerations in mind, the dosage unit for a particular patient can be readily determined by the medical practitioner in accordance with the techniques known in the medical arts.

BRIEF DESCRIPTION OF THE DRAWINGS

FIG. 2 shows a Table with Anticancer activity results;

FIG. 3 shows a Table with Antimalarial activity results; and

FIG. 4 shows a Table with Antileishmanial activity results.

Figure 1:
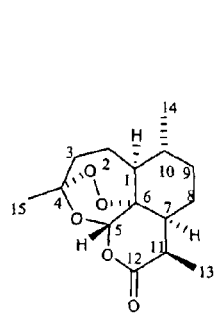
FIG. 1 shows the chemical structures of compounds of the application.
Figure 1:
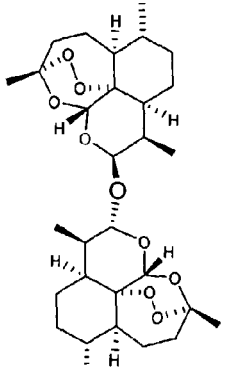
Figure 1:
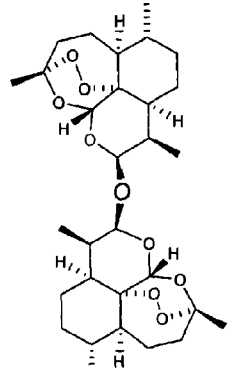
Figure 1:
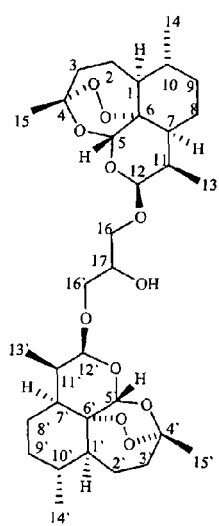
Figure 1:
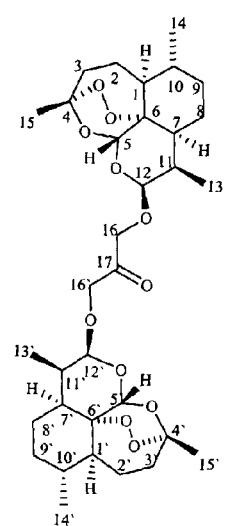
Figure 1:
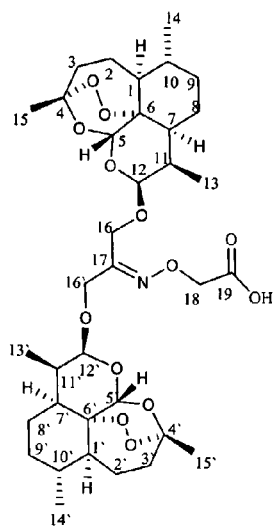
Figure 1:
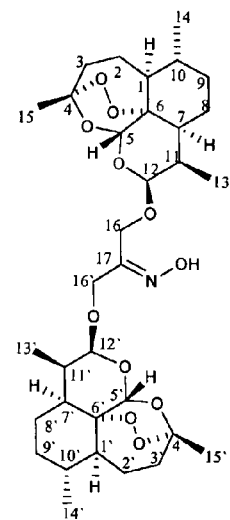
Figure 1:
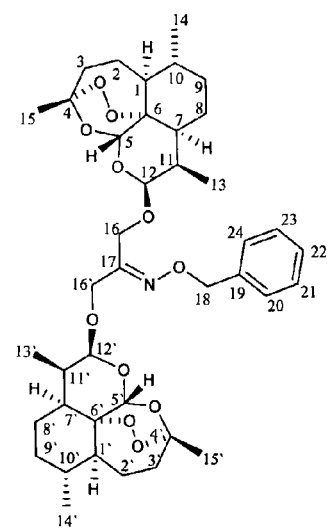
Figure 1:
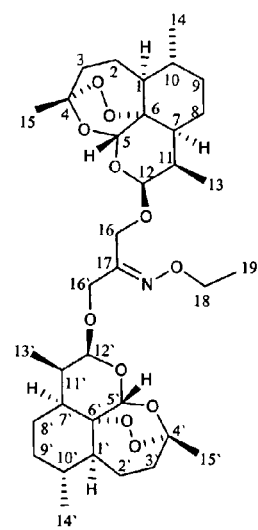
Figure 1:
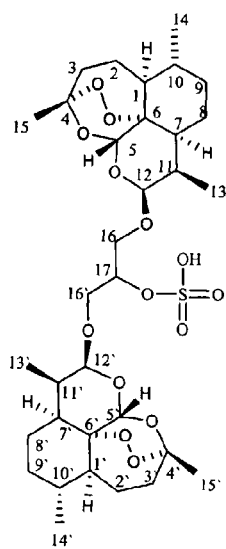
Figure 1:
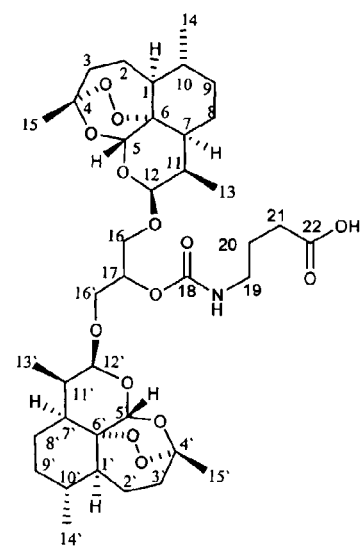
Figure 1:
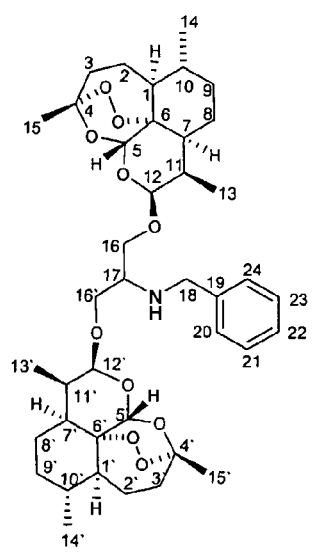
Figure 1:
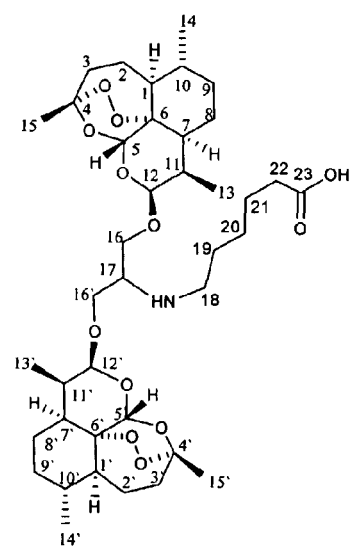

The compounds of this invention have been prepared by reaction of dihydroartemisinin or dihydroartemisitene with dihydroxy acetone to produce the dimeric ketone under acidic conditions (borontrifluoride etherate) in dry ether followed by subsequent functionalization of the purified ketone dimer to produce the desired product. Optional functionalizations include, for example, the preparation of oximes, amines, substituted alcohols with different functionalities or reduction of the ketone dimer to its dihydro derivative (alcohol) followed by functionalization of the resulting OH group to produce a variety of ester, carbamates, sulfates, phosphates, etc. . . . The starting material (dihydroartemisinin) is prepared by sodium borohydride reduction of the natural product artemisinin (1). The latter compound is isolated from the leaves of *Artemisia annua* following the procedures previously described (16, 17). Similarly, dihydroartemisitene is derived from artemisitene, a constituent of the same plant. The compounds of the invention were tested for anti-tumor activity and in the anti-malarial and anti-Leishmanial screens. The activities are shown in Tables 1-3.

EXAMPLES

Reactions were run in oven dried round-bottomed flasks. Diethyl ether (ether) was distilled from sodium benzophenone ketyl prior to use under an atmosphere of argon. All chemicals were purchased from Sigma-Aldrich and used without further purification. Artemisinin (1) was isolated from locally grown *Artemisia annua* L. plants, using a literature procedure (16, 17), and was reduced to dihydroartemisinin as previously reported (18).

Column chromatography was performed using flash chromatography, using silica gel purchased from Merck (particle size 230-400 mesh). Analytical thin-layer chromatography (TLC) was performed with silica gel 60 $F_{254}$ plates (250 μm thickness; Merck), using n-hexane-EtOAc or $CH_2CL_2$-EtOAc mixtures or other solvent systems as needed. Visualization was accomplished by spraying with p-anisaldehyde spray reagent followed by heating using a hot-air gun (19) or with a solution of $H_2SO_4$ in EtoH followed by heating.

Spectral data were obtained as follows. 1D and 2D NMR spectra were obtained on Bruker Avance DRX 500 spectrometers at 500 MHz ($^1H$) and 125 MHz ($^{13}C$) or Bruker DRX 400 spectrometer using the solvent peak as the internal standard. HREIMS were obtained using an Agilent Time-Of-Flight LCMS.

Example 1

Preparation of the Oxime of the β,β-Dihydroartemisinin Dimer with Dihydroxyacetone (6)

β,β-Dihydroartemisinin dimer with dihydroxyacetone (4) (50 mg, 0.08 mmol), sodium acetate (40 mg, 0.48 mmol) and aminoxy-acetic acid (9.1 mg, 0.10 mmol, 1.2 eq) were mixed in 5 ml of dichloromethane (freshly distilled) and the mixture refluxed for 4 hours under argon. TLC indicated the completion of the reaction.

The resulting reaction product was evaporated to dryness, the residue dissolved in 6 ml of ethyl acetate, washed with water, dried over anhydrous sodium sulphate and the solvent evaporated to dryness.

The residue was chromatographed on silica gel column (300 mg) and eluted with chloroform with polarity increasing to 90:10 chloroform:methanol. Fractions were collected and combined according to TLC similarities to give one major fraction having the desired product (41.1 mg), with spectral data consistent with structure 6.

$^1$H-NMR in $CDCl_3$ at 400 MHz: δ 8.23 (1H, br s, OH); 5.41 and 5.38 (1H each, s each, H-5 and H-5'); 4.85 and 4.81 (1H each, d each, J=3.2 Hz each, H-12 and H-12'); 4.65 and 4.38 (2H each, br d each, J=14.8 and 15.6 Hz, respectively, H-16 and H-16'); 4.62 (2H, s, H-18); 2.63, (2H, br m, H-11 and H-11'); 2.34 and 2.01 (2H each, br t and br d, respectively, J=13.6 and 14.4 Hz, respectively, H-3 and H-3'); 1.85 and 1.50 (2H each, m each, H-2 and H-2'); 1.73 (4H, br t, J=11.2 Hz, H-9 and H-9'); 1.61 and 1.46 (4H each, m each, H-7 and H-7', H-8 and H-8', and H-10 and H-10'); 1.41 (6H, s, Me-15 and Me-15'); 1.22 (2H, m, H-1 and H-1'); 0.94-0.82 (12H, Me-13 and Me-13', and Me-14 and Me-14').

$^{13}$C-NMR in $CDCl_3$ at 100 MHz: δ 174.10 (s, C=O); 156.78 (s, C=N); 104.20 and 104.14 (s, C-4 and C-4'); 102.34 and 100.73 (d, C-12 and C-12'); 87.97 (d, C-5 and C-5'); 81.04 and 80.96 (s, C-6 and C-6'); 70.35 (t, C-18); 64.69 and 61.59 (t, C-16 and C-16'); 52.47 (d, C-1 and C-1'); 44.29 (d, C-7 and C-7'); 37.42 (d, C-10 and C-10'); 36.36 (t, C-3 and C-3'); 34.59 (t, C-9 and C-9'); 30.80 (d, C-11 and C-11'); 26.06 and 26.03 (q, C-15 and C-15'); 24.46 (t, C-2 and C-2'); 24.41 (t, C-8 and C-8'); 20.36 (q, C-14 and C-14'); 12.96 (q, C-13 and C-13').

HREIMS: (m/z) 718.3190 [M+Na], (calcd. for $C_{35}H_{53}NO_{13}$, 695.3517).

Example 2

Preparation of the Oxime of the β,β-Dihydroartemisinin Dimer with Dihydroxyacetone (7)

β,β-Dihydroartemisinin dimer with dihydroxyacetone (4) (100 mg, 0.16 mmol), sodium acetate (80 mg, 0.48 mmol) and hydroxylamine hydrochloride (14 mg, 0.20 mmol, 1.3 eq) were mixed in 10 ml of dichloromethane (freshly distilled) and refluxed for 0.5 hours under argon. TLC indicated the completion of the reaction.

The resulting reaction product was evaporated to dryness, the residue dissolved in 6 ml of ethyl acetate, washed with water, dried over anhydrous sodium sulphate and the solvent evaporated to dryness.

The residue was chromatographed on silica gel column and eluted with hexane:ethyl acetate (90:10) with polarity increasing to 70:30. Fractions were collected and combined according to TLC similarities to give one major fraction having the desired product (76.0 mg), with spectral data consistent with structure 7.

$^1$H-NMR in $CDCl_3$ at 400 MHz: δ 5.42 (2H, s, H-5 and H-5'); 4.84 and 4.80 (1H each, d each, J=2.4 Hz each, H-12 and H-12'); 4.65, 4.39, 4.37 and 4.16 (1H each, d each, J=14.0, 11.6, 14.0 and 12.0 Hz, respectively, H-16 and H-16'); 2.66, (2H, m, H-11 and H-11'); 2.38 and 2.03 (2H each, ddd and br d, respectively, J=2.8 Hz each, H-3 and H-3'); 1.87 and 1.51 (2H each, m each, H-2 and H-2'); 1.74 (4H, m, H-9 and H-9'); 1.62 and 1.48 (4H each, m each, H-7 and H-7', H-8 and H-8', and H-10 and H-10'); 1.43 (6H, s, Me-15 and Me-15'); 1.26 (2H, m, H-1 and H-1'); 0.96-0.89 (12H, Me-13 and Me-13', and Me-14 and Me-14').

$^{13}$C-NMR in $CDCl_3$ at 100 MHz: δ 155.21 (s, C=N); 104.16 and 104.13 (s, C-4 and C-4'); 102.48 and 101.05 (d, C-12 and C-12'); 87.93 (d, C-5 and C-5'); 81.02 and 80.98 (s, C-6 and C-6'); 64.42 and 60.24 (t, C-16 and C-16'); 52.55 (d, C-1 and C-1'); 44.38 (d, C-7 and C-7'); 37.44 and 37.39 (d, C-10 and C-10'); 36.43 (t, C-3 and C-3'); 34.66 (t, C-9 and C-9'); 30.87 and 30.72 (d, C-11 and C-11'); 26.05 (q, C-15 and C-15'); 24.64 (t, C-2 and C-2'); 24.52 (t, C-8 and C-8'); 20.32 (q, C-14 and C-14'); 13.06 and 12.96 (q, C-13 and C-13').

HREIMS: (m/z) 660.3343 [M+Na], 676.3058 [M+K], (calcd. for $C_{33}H_{51}NO_{11}$, 637.3462).

Example 3

Preparation of the Oxime of the β,β-Dihydroartemisinin Dimer with Dihydroxyacetone (8)

β,β-Dihydroartemisinin dimer with dihydroxyacetone (4) (100 mg, 0.16 mmol), sodium acetate (80 mg, 0.48 mmol) and O-benzyl hydroxylamine hydrochloride (28.1 mg, 0.18 mmol, 1.1 eq) were mixed in 5 ml of dichloromethane (freshly distilled) and refluxed for 18 hours under argon. TLC indicated the completion of the reaction.

The resulting reaction product was evaporated to dryness, the residue dissolved in 6 ml of ethyl acetate, washed with water, dried over anhydrous sodium sulphate and the solvent evaporated to dryness.

The residue was chromatographed on silica gel column and eluted with dichloromethane with polarity increasing to 90:10 dichloromethane:ethyl acetate. Fractions were collected and combined according to TLC similarities to give one major fraction having the desired product (64 mg), with spectral data consistent with structure 8.

$^1$H-NMR in $CDCl_3$ at 400 MHz: δ 7.35 (5H, m, H-20 to H-24); 5.43 and 5.39 (1H each, s each, H-5 and H-5'); 5.12 (2H, s, H-18); 4.86 and 4.80 (1H each, d each, J=3.2 Hz each, H-12 and H-12'); 4.67, 4.42, 4.35 and 4.20 (1H each, d each, J=14.4, 12.0, 14.0 and 12.4 Hz, respectively, H-16 and H-16'); 2.65, (2H, m, H-11 and H-11'); 2.38 and 2.05 (2H each, br t and br d, respectively, J=14.0 and 11.6 Hz, respectively, H-3 and H-3'); 1.86 and 1.49 (2H each, m each, H-2 and H-2'); 1.73 (4H, m, H-9 and H-9'); 1.60 and 1.48 (4H each, m each, H-7 and H-7', H-8 and H-8', and H-10 and H-10'); 1.44 (6H, s, Me-15 and Me-15'); 1.26 (2H, m, H-1 and H-1'); 0.97-0.92 (12H, Me-13 and Me-13', and Me-14 and Me-14').

$^{13}$C-NMR in $CDCl_3$ at 100 MHz: δ 155.00 (s, C=N); 137.66 (s, C-19); 128.31 (d, C-20 and C-24); 127.96 (d, C-21 and C-23); 127.76 (d, C-22); 104.06 and 104.03 (s, C-4 and C-4'); 102.49 and 100.93 (d, C-12 and C-12'); 87.95 and 87.91 (d, C-5 and C-5'); 81.02 and 80.94 (s, C-6 and C-6'); 76.23 (t, C-18); 65.27 and 61.75 (t, C-16 and C-16'); 52.59 and 52.55 (d, C-1 and C-1'); 44.42 and 44.41 (d, C-7 and C-7'); 37.39 and 37.37 (d, C-1 and C-10'); 36.47 and 36.45 (t, C-3 and C-3'); 34.70 and 34.65 (t, C-9 and C-9'); 30.87 and 30.74 (d, C-11 and C-11'); 26.15 and 26.14 (q, C-15 and C-15'); 24.64 and 24.63 (t, C-2 and C-2'); 24.49 and 24.43 (t, C-8 and C-8'); 20.36 (q, C-14 and C-14'); 13.06 and 12.96 (q, C-13 and C-13').

HREIMS: (m/z) 750.3841 [M+Na], (calcd. for $C_{40}H_{57}NO_{11}$, 727.3932).

Example 4

Preparation of the Oxime of the β,β-Dihydroartemisinin Dimer with Dihydroxyacetone (9)

β,β-Dihydroartemisinin dimer with dihydroxyacetone (4) (100 mg, 0.16 mmol), sodium acetate (80 mg, 0.48 mmol) and O-ethyl hydroxylamine hydrochloride (17.0 mg, 0.17 mmol, 1.1 eq) were mixed in 5 ml of dichloromethane (freshly distilled) and refluxed for 5.5 hours under argon. TLC indicated the completion of the reaction.

The resulting reaction product was evaporated to dryness, the residue dissolved in 6 ml of ethyl acetate, washed with water, dried over anhydrous sodium sulphate and the solvent evaporated to dryness.

The residue was chromatographed on silica gel column and eluted with dichloromethane with polarity increasing to 90:10 dichloromethane:ethyl acetate. Fractions were collected and combined according to TLC similarities to give one major fraction having the desired product (51.7 mg), with spectral data consistent with structure 9.

$^1$H-NMR in $CDCl_3$ at 400 MHz: δ 5.36 and 5.32 (1H each, s each, H-5 and H-5'); 4.79 and 4.72 (1H each, d each, J=3.2 and 2.8 Hz, respectively, H-12 and H-12'); 4.52, 4.31, 4.23 and 4.09 (1H each, d each, J=14.4, 12.0, 14.0 and 12.0 Hz, respectively, H-16 and H-16'); 4.02 (2H, q, J=7.2 Hz, H-18); 2.57, (2H, m, H-11 and H-11'); 2.29 and 1.94 (2H each, br t and br d, respectively, J=14.0 and 10.4 Hz, respectively, H-3 and H-3'); 1.78 and 1.49 (2H each, br m each, H-2 and H-2'); 1.78 (4H, m, H-9 and H-9'); 1.68 and 1.40 (4H each, m each, H-7 and H-7', H-8 and H-8', and H-10 and H-10'); 1.35 (6H, s, Me-15 and Me-15'); 1.26 (2H, m, H-1 and H-1'); 1.18 (3H, t, J=6.8 Hz, Me-19); 0.89-0.81 (12H, Me-13 and Me-13', and Me-14 and Me-14').

$^{13}$C-NMR in CDCl$_3$ at 100 MHz: δ 153.94 (s, C=N); 103.94 and 103.89 (s, C-4 and C-4'); 102.37 and 100.71 (d, C-12 and C-12'); 87.83 and 87.81 (d, C-5 and C-5'); 80.90 and 80.83 (s, C-6 and C-6'); 65.22 and 62.59 (t, C-16 and C-16'); 69.68 (t, C-18); 52.50 and 52.48 (d, C-1 and C-1'); 44.35 and 44.31 (d, C-7 and C-7'); 37.37 and 37.33 (d, C-10 and C-10'); 36.37 and 36.35 (t, C-3 and C-3'); 34.64 and 34.60 (t, C-9 and C-9'); 30.79 and 30.67 (d, C-11 and C-11'); 26.04 (q, C-15 and C-15'); 24.60 (t, C-2 and C-2'); 24.42 and 24.35 (t, C-8 and C-8'); 20.30 (q, C-14 and C-14'); 14.49 (q, C-19); 13.04 and 12.95 (q, C-13 and C-13').

HREIMS: (m/z) 688.3704 [M+Na], (calcd. for C$_{35}$H$_{55}$NO$_{11}$, 665.3775).

Example 5

Preparation of the Sulphate of the β,β-Dihydroartemisinin Dimer with Glycerol (10)

β,β-Dihydroartemisinin dimer with glycerol (5) (90 mg, 0.14 mmol) was dissolved in 2.5 ml of pyridine. Temperature was adjusted to −18° C. at which time 10 eq. of chlorosulfonic acid was added (as reaction is very violent, chlorosulfonic acid was added dropwise). After complete addition of chlorosulfonic acid the mixture was allowed to stir overnight at room temperature under argon. In the morning, TLC indicated the completion of the reaction. Acetic acid was added to the reaction mixture and the product was extracted with 3×30 ml of dichloromethane, dried over anhydrous sodium sulfate and evaporated to dryness.

The residue was chromatographed on silica gel column and eluted with ethyl acetate with polarity increasing to 80:20 ethyl acetate:methanol. Fractions were collected and combined according to TLC similarities to give one major fraction having the desired product (39.2 mg), with spectral data consistent with structure 10.

$^1$H-NMR in CDCl$_3$ at 400 MHz: δ 5.45 (1H, s, H-17); 5.38 and 5.27 (1H each, s each, H-5 and H-5'); 4.86 and 4.78 (1H each, s each, H-12 and H-12'); 4.07 (4H, br t, J=6.8 Hz, H-16 and H-16'); 2.56, (2H, m, H-11 and H-11'); 2.30 and 2.01 (2H each, br t each, J=12.0 Hz each, H-3 and H-3'); 1.82 and 1.60 (2H each, m each, H-2 and H-2'); 1.72 (4H, br t, J=10.2 Hz, H-9 and H-9'); 1.71 and 1.62 (4H each, m each, H-7 and H-7', H-8 and H-8', and H-10 and H-10'); 1.39 (6H, s, Me-15 and Me-15'); 1.22 (2H, m, H-1 and H-1'); 0.91-0.86 (12H, Me-13 and Me-13', and Me-14 and Me-14').

$^{13}$C-NMR in CDCl$_3$ at 100 MHz: δ 104.38 and 104.20 (s, C-4 and C-4'); 102.48 and 101.71 (d, C-12 and C-12'); 88.05 and 87.94 (d, C-5 and C-5'); 81.04 and 80.99 (s, C-6 and C-6'); 76.13 (d, C-17); 65.96 and 65.72 (t, C-16 and C-16'); 52.61 and 52.56 (d, C-1 and C-1'); 44.46 and 44.40 (d, C-7 and C-7'); 37.23 (d, C-10 and C-10'); 36.44 and 36.36 (t, C-3 and C-3'); 34.69 (t, C-9 and C-9'); 30.89 and 30.82 (d, C-11 and C-11'); 25.97 and 25.85 (q, C-15 and C-15'); 24.61 (t, C-2 and C-2'); 24.45 (t, C-8 and C-8'); 20.37 (q, C-14 and C-14'); 12.98 (q, C-13 and C-13').

HREIMS: (m/z) 703.2942 [M−H], (calcd. for C$_{35}$H$_{52}$SO$_{14}$, 704.3078).

Example 6

Preparation of the Carbamate of the β,β-Dihydroartemisinin Dimer with Glycerol (11)

β,β-Dihydroartemisinin dimer with glycerol (5) (200 mg, 0.32 mmol) was dissolved in 5.0 ml of dichloromethane and 4-nitrophenyl chloroformate (1.1 eq.) was added to it. The reaction was allowed to run under argon at room temperature overnight and 1.1 eq. of 4-amino butyric acid allyl ester was added to it. The reaction was stirred for 24 hours and continuous monitoring of TLC indicated no more conversion of starting material to the Example 6

Preparation of the Carbamate of the β,β-Dihydroartemisinin Dimer with Glycerol (11)

β,β-Dihydroartemisinin dimer with glycerol (5) (200 mg, 0.32 mmol) was dissolved in 5.0 ml of dichloromethane and 4-nitrophenyl chloroformate (1.1 eq.) was added to it. The reaction was allowed to run under argon at room temperature overnight and 1.1 eq. of 4-amino butyric acid allyl ester was added to it. The reaction was stirred for 24 hours and continuous monitoring of TLC indicated no more conversion of starting material to the protected product. The solvent was evaporated and the protected carbamate dimer was purified (135 mg) on silica gel column (10% EtOAc:DCM).

The protected carbamate dimer was dissolved in 5 ml of dichloromethane and 0.05 eq. of phenyl silane and 0.005 eq. of Tetrakis triphenyl phosphine palladium was added to it. The reaction was allowed to run at room temperature for 3 hours at which time 1 ml of methanol was added and stirred for another 10 minutes.

The solvent was evaporated and the residue was chromatographed on silica gel column and eluted with 30:70 ethyl acetate:dichloromethane with polarity increasing to 20:80 ethyl acetate:methanol. Similar fractions were combined to give one major fraction having the desired product (78 mg), with spectral data consistent with structure 11.

$^1$H-NMR in CDCl$_3$ at 400 MHz: δ 5.40 and 5.34 (1H each, s each, H-5 and H-5'); 5.27 (2H, s, H-12 and H-12'); 4.76 (1H, br dd, J=2.4 Hz, H-17); 3.88 and 3.53 (2H each, br dd each, J=4.4 Hz, H-16 and H-16'); 3.18 (2H, q, J=6.4 Hz, H-19); 2.57, (2H, br s, H-11 and H-11'); 2.35 and 1.99 (2H each, m each, H-3 and H-3'); 2.29 (2H, m, H-21); 1.80 and 1.58 (2H each, m each, H-2 and H-2'); 1.78 (6H, m, H-9 and H-9', and H-20); 1.70 and 1.40 (4H each, m each, H-7 and H-7', H-8 and H-8', and H-10 and H-10'); 1.38 (6H, s, Me-15 and Me-15'); 1.20 (2H, m, H-1 and H-1'); 0.92-0.84 (12H, Me-13 and Me-13', and Me-14 and Me-14').

$^{13}$C-NMR in CDCl$_3$ at 100 MHz: δ 177.16 (s, C-22); 155.90 (s, C-18); 104.16 and 104.08 (s, C-4 and C-4'); 102.62 and 102.18 (d, C-12 and C-12'); 87.93 and 87.87 (d, C-5 and C-5'); 81.04 and 81.00 (s, C-6 and C-6'); 71.90 (d, C-17); 67.71 and 66.63 (t, C-16 and C-16'); 52.51 (d, C-1 and C-1'); 44.36 (d, C-7 and C-7'); 40.33 (t, C-19); 37.41 and 37.38 (d, C-10 and C-10'); 36.40 (t, C-3 and C-3'); 34.60 (t, C-9 and C-9'); 31.15 (t, C-21); 30.80 (d, C-11 and C-11'); 26.05 (q, C-15 and C-15'); 24.93 (t, C-20); 24.62 (t, C-2 and C-2'); 24.40 (t, C-8 and C-8'); 20.34 and 20.30 (q, C-14 and C-14'); 12.90 (q, C-13 and C-13').

HREIMS: (m/z) 776.3936 [M+Na], (calcd. for C$_{38}$H$_{59}$NO$_4$, 753.3936).

Example 7

Preparation of the Benzyl Amine of the β,β-Dihydroartemisinin Dimer with Dihydroxy Acetone (12)

β,β-Dihydroartemisinin dimer with dihydroxy acetone (4) (15 mg, 0.02 mmol) was dissolved in 1.5 ml of dichloroethane and benzyl amine (1 eq) was added to it. Sodium triacetoxy borohydride (1 eq) and AcOH (1 eq) were added and the reaction was allowed to run under argon at room temperature for 72 hours with continuous monitoring with TLC. 1N NaOH was added to quench the reaction and the mixture shaken with ether (3×10 ml). The organic layer was dried over anhydrous sodium sulphate and evaporated to dryness.

The residue was chromatographed on silica gel column and eluted with ethyl acetate with polarity increasing to 30:70 ethyl acetate:dichloromethane. Fractions were collected and similar fractions were combined to give one major fraction having the desired product (7.9 mg), with spectral data consistent with structure 12.

$^1$H-NMR in CDCl$_3$ at 400 MHz: δ 7.33 (3H, s, H-20, H-21 and H-23); 7.32 (1H, s, H-24); 7.27 (1H, s, H-22); 5.40 and 5.39 (1H each, s each, H-5 and H-5'); 4.82 (2H, br t, J=4.8 Hz, H-12 and H-12'); 3.86 (2H, d, J=2.4 Hz, H-18); 3.95 and 3.45 (2H each, m and dd, J=4.6 Hz, H-16 and H-16'); 3.01 (1H, m, H-17); 2.66, (2H, m, H-11 and H-11'); 2.38 and 2.06 (2H each, ddd and m, J=3.6 Hz, H-3 and H-3'); 1.89 (4H, m, H-9 and H-9'); 1.88 and 1.62 (2H each, m each, H-2 and H-2'); 1.74 and 1.48 (4H each, m each, H-7 and H-7', H-8 and H-8', and H-10 and H-10'); 1.45 (6H, s, Me-15 and Me-15'); 1.28 (2H, m, H-1 and H-1'); 0.96-0.91 (12H, Me-13 and Me-13', and Me-14 and Me-14').

$^{13}$C-NMR in CDCl$_3$ at 100 MHz: δ 140.57 (s, C-19); 128.96 (d, C-21 and C-23); 128.38 (d, C-20 and C-24); 126.93 (d, C-22); 104.05 (s, C-4 and C-4'); 102.61 and 102.38 (d, C-12 and C-12'); 87.91 (d, C-5 and C-5'); 81.02 (s, C-6 and C-6'); 68.17 (t, C-16 and C-16'); 56.61 (d, C-17); 52.59 (d, C-1 and C-1'); 51.50 (t, C-18); 44.41 and 44.39 (d, C-7 and C-7'); 37.37 and 37.34 (d, C-1 and C-10'); 36.51 (t, C-3 and C-3'); 34.60 (t, C-9 and C-9'); 30.98 and 30.94 (d, C-11 and C-11'); 26.20 (q, C-15 and C-15'); 24.60 (t, C-2 and C-2'); 24.65 (t, C-8 and C-8'); 20.36 (q, C-14 and C-14'); 13.13 and 13.11 (q, C-13 and C-13').

HREIMS: (m/z) 714.5016 [M+H], 736.4081 [M+Na], (calcd. for C$_{40}$H$_{59}$NO$_{10}$, 713.4139).

Example 8

Preparation of the Amino Hexanoic Acid Derivative of the β,β-Dihydroartemisinin Dimer with Dihydroxy Acetone (13)

β,β-Dihydroartemisinin dimer with dihydroxy acetone (4) (15 mg, 0.02 mmol) was dissolved in 1.5 ml of THF and 6-amino hexanoic acid (1 eq) was added. Sodium triacetoxy borohydride (1 eq) and AcOH (1 eq) were then added and the reaction was allowed to run under argon at room temperature for 4 hours with continuous monitoring on TLC. 1N NaOH was added to quench the reaction and then the mixture shaken with ether (3×10 ml) and DCM (3×10 ml). The organic layers were combined and dried over anhydrous sodium sulphate and evaporated to dryness.

The residue was chromatographed on silica gel column and eluted with ethyl acetate with polarity increasing to 30:70 methanol:ethyl acetate. Fractions were collected and similar fractions were combined to give one major fraction having the desired product (7.3 mg), with spectral data consistent with structure 13.

$^1$H-NMR in CDCl$_3$ at 400 MHz: δ 5.41 and 5.40 (1H each, s each, H-5 and H-5'); 4.84 (2H, s, H-12 and H-12'); 4.15 and 3.75 (2H each, m each, H-16 and H-16'); 3.42 (1H, m, H-17); 2.67, (2H, m, H-11 and H-11'); 2.35 (4H, m, H-3 and H-3'); 1.88 and 1.50 (2H each, m each, H-2 and H-2'); 1.78 (4H, br s, H-8 and H-8'); 1.42 (6H, s, Me-15 and Me-15'); 1.27 (2H, m, H-1 and H-1'); 0.97-0.92 (12H, Me-13 and Me-13', and Me-14 and Me-14').

$^{13}$C-NMR in CDCl$_3$ at 100 MHz: δ 104.16 (s, C-4 and C-4'); 103.02 and 102.63 (d, C-12 and C-12'); 88.02 and 87.96 (d, C-5 and C-5'); 80.90 (s, C-6 and C-6'); 65.84 and 65.73 (t, C-16 and C-16'); 56.80 (d, C-17); 52.51 (d, C-1 and C-1'); 44.16 (t, C-18); 44.23 (d, C-7 and C-7'); 37.24 and 37.19 (d, C-10 and C-10'); 36.46 (t, C-3 and C-3'); 34.59 (t, C-9 and C-9'); 30.78 and 30.71 (d, C-11 and C-11'); 26.05 (q, C-15 and C-15'); 24.56 (t, C-2 and C-2'); 20.36 and 20.39 (q, C-14 and C-14'); 13.03 (q, C-13 and C-13').

HREIMS: (m/z) 738.4469 [M+H], 760.4274 [M+Na], (calcd. for C$_{39}$H$_{63}$NO$_{12}$, 737.4350).

Example 9

Anticancer Activity of Compounds 6-13

The anticancer activity of compounds 6-13 was evaluated at the National Center for Natural Products Research (NCNPR) against the following cell lines:

SK-MEL (Human Malignant Melanoma); KB (Human Epidermal Carcinoma, oral); BT 549 (Breast Ductal Carcinoma); and SK-OV3 (Human Ovary Carcinoma). Cytotoxicity was evaluated in two cell lines, namely Vero cells (Monkey Kidney Fibroblast) and LLC-PK1 (Pig Kidney Epithelial).

The results of the testing are summarized in table 1.

Example 10

Antimalarial Activity of Compounds 6-11

The antimalarial activity of compounds 6-11 was evaluated on the antimalarial screen carried out at the NCNPR. The compounds were tested against two stains of the malaria parasite namely the D6 clone and the W2 clone of *Plasmodium folciparum*, with cytotoxicity evaluated using Vero cells. The activities of these compounds are presented in table 2.

Example 11

Antileishmanial Activity of Compounds 6-13

The activity of compounds 6-13 against the leishmanial parasite was evaluated at the NCNPR. The activity of these compounds are shown in table 3.

LITERATURE CITED

1 American Cancer Society, Statistics for 2001. (http://www.cancer.org/downloads/STT/F&F2001.pdft)
2. Cragg, G. M., Newman, D. J., Snader, K. M.: Natural products in drug discovery and development. *J. Nat. Prod.*, 60:52-60 (1997).
3. Shu Y. Z.: Recent natural products based drug development: a pharmaceutical industry perspective. *J. Nat. Prod.*, 61:1053-1071 (1998).
4. Cragg, G. M., Newman, D. J., Weiss, R. B.; Coral reefs, forests, and thermal vents: the worldwide exploration of nature for novel antitumor agents. *Seminar Oncol* 24:156-163 (1997).
5. Clark, A. M.: Natural products as a resource for new drugs. *Pharmaceut Res* 13:1133-1141 (1996).
6. Report of the Coordinating Group for Research on the Structure of Qing Hao Su. K'O Hsueh T'Ung Pao 22, 142 (1977); Chem. Abstr. 87, 98788g (1977).
7. Beekman, A. C., Barentsen, A. R. W., Woerdengag, H. J., Van Uden, W., Pras, N., El-Feraly, F. S., and Galal, A. M. Stereochemistry-dependent cytotoxicity of some artemisinin derivatives; *J. Nat. Prod.*, 60: 325 (1997).
8. Zheng, G. Q; Cytotoxic terpenoids and flavonoids from *Artemisia annua, Planta Medica,* 60 (1): 54-7 (1994).

9. Woerdenbag, H. J., Moskal, T. A., Pras, N., Malingre, T. M., Kampinga, H. H., Konings, A. W. T., and El-Feraly, F. S., Cytotoxicity of artemisinin-related endoperoxides to Ehrlich ascites tumor cells, *J. Nat. Prod,* 56: 84a (1993).
10. Beekman, A. C., Woerdenbag, H. J., Kampigna, H. H., and Konings, A. W. T.; Sterochemistry-dependent cytotoxicity of some artemisinin derivatives, *Phytother. Res.,* 10, 140 (1996).
11. Posner, G. H., et al; Trioxane Dimers Have Potent Antimalarial, Anti-proliferative, and Anti-tumor Activities In Vitro, *Bioorganic and Med. Chem.,* 5:1257-65 (1997).
12. Posner, G. H., Ploypradith, P., Parker, M. H., O'Dowd, H., Woo, S.-H., Northrop, J., Krasavin, M., Dolan, P., Kensler, T. W., Xie, S., and Shapiro, T. A.; Antimalarial, Anti-proliferative, and Anti-tumor Activities of Artemisinin-Derived, Chemically Robust, Trioxane Dimers, *J. Med. Chem.,* 42, 4275-80 (1999).
13. Zhang and Darbie, U.S. Pat. No. 5,677,468 (1997).
14. Zhang and Darbie, U.S. Pat. No. 5,856,351 (1999).
15. ElSohly, M. A., Ross, S. A., and Galal, A. M.; U.S. Pat. No. 6,790,863 B2 (2004).
16. ElSohly, H. N., Croom, E. M., El-Feraly, F. S., and El-Sheri, M. M., *J. Nat. Prod.,* 53(6):1560-4 (1990).
17. ElSohly, H. N, and El-Feraly, F. S., U.S. Pat. No. 4,952,603 (1990).
18. Lin, A. J., Klyman, D. L., and Milhous, W. K., J. Med. Chem. 30, 2147 (1987).
19. El-Feraly, F. S., and Hufford, C. D., J. Org. Chem., 47, 1527 (1982).
20. El-Feraly, F. S., Ayalp, A., Al-Yahia, M. A., McPhail, D. R. and McPhail, A. T., *J. Nat. Prod.,* 53 (1), 66-71 (1990).

We claim:

1. A method of treating cancer or inhibiting cancer metastasis comprising administering to a subject suffering from cancer an effective amount of at least one compound of the formula:

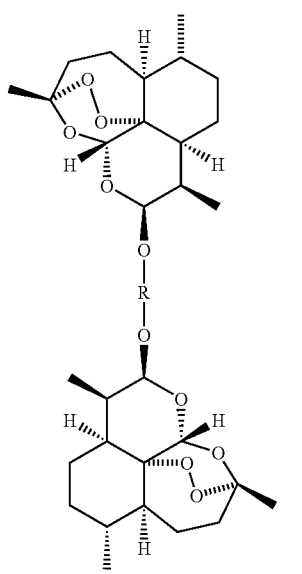

Where R is:

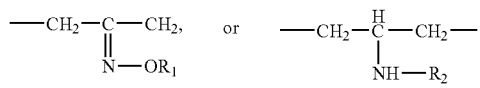

where $R_1$ is H or alkyl, cycloalkyl or aryl moiety, free or containing one of a variety of functional groups such as COOH, OH, NH or derivatives thereof;

where $R_2$ is H or alkyl, cycloalkyl or aryl moiety, free or containing one of a variety of functional groups such as COOH, OH, NH or derivatives thereof;

or a compound of the formula

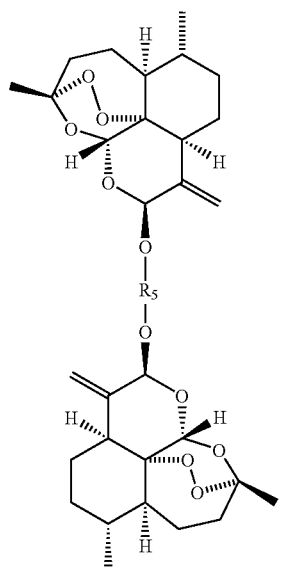

where $R_5$ is selected from one of the substituents described above for R.

2. A method of treating a protozoal infection comprising administering to a subject suffering from an infection an effective amount of at least one compound of the formula:

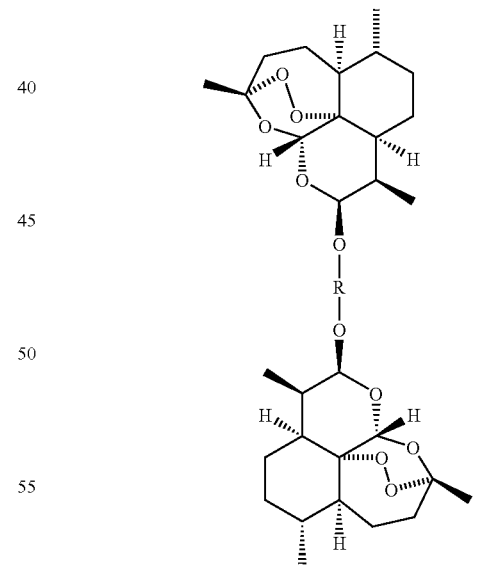

where R is

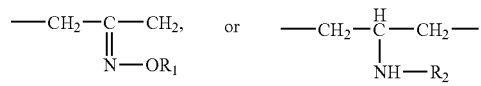

where $R_1$ is H or alkyl, cycloalkyl or aryl moiety, free or containing one of a variety of functional groups such as COOH, OH, NH or derivatives thereof;

where $R_2$ is H or alkyl, cycloalkyl or aryl moiety, free or containing one of a variety of functional groups such as COOH, OH, NH or derivatives thereof;

or a compound of the formula:

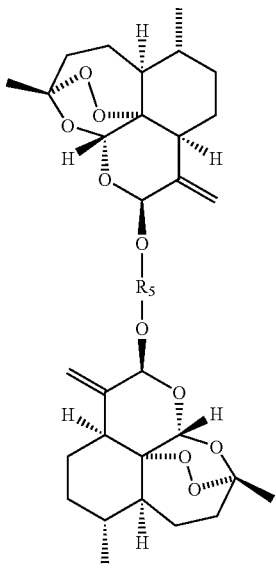

where $R_5$ is selected from one of the substituents described above for R.

3. A compound of the formula

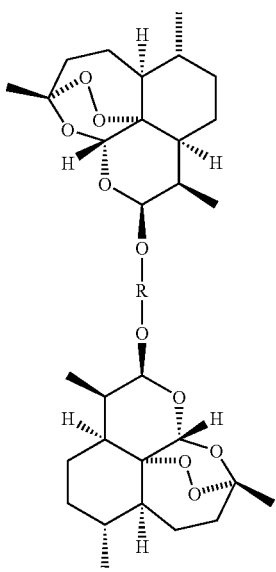

where R is

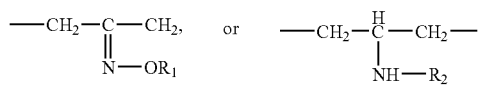

Where $R_1$ is H or alkyl, cycloalkyl or aryl moiety, free or containing one of a variety of functional groups such as COOH, OH, NH or derivatives thereof;

where $R_2$ is H or alkyl, cycloalkyl or aryl moiety, free or containing one of a variety of functional groups such as COOH, OH, NH or derivatives thereof;

or a compound of the formula

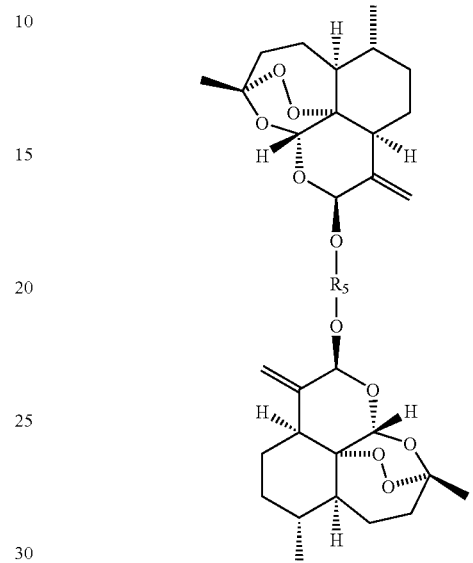

where $R_5$ is selected from one of the substituents described above for R.

4. A pharmaceutical composition comprising at least of one compound according to claim 3 and a pharmaceutically acceptable carrier and/or excipient.

5. A method of preparing compounds of the formulas of claim 3, comprising reacting dihydroartemisinin or dihydroartemisitene with dihydroxy acetone under acidic conditions such as borontrifluoride etherate followed by additional functionalization of the resulting ketone dimer.

6. The method of claim 5 where R is

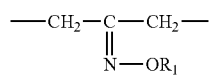

residue and $R_1$ is selected from H, or alkyl, cycloalkyl or aryl groups free or containing one of a variety of functional groups such as COOH, OH or NH or derivatives thereof comprising reacting the ketone dimer of claim 5 with $NH_2$—O—$R_1$ (where $R_1$ is the appropriate substituent) under basic conditions followed by purification of the reaction mixture to separate the purified oxime.

7. The method of claim 5 where R is

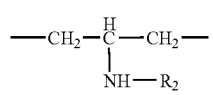

residue and $R_2$ is selected from H, or alkyl, cycloalkyl or aryl groups free or containing one of a variety of functional groups such as COOH, OH or NH or derivatives thereof comprising reacting the ketone dimer of claim 5 with $NH_2$—$R_2$ (where $R_2$ is the appropriate substituent) and sodium cyanoborohydride or sodium triacetoxyborohydride, followed by purification of the reaction mixture to separate the purified amine.

8. The method of claim 5 where R5 is

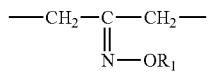

residue and $R_1$ is selected from H, or alkyl, cycloalkyl or aryl groups free or containing one of a variety of functional groups such as COOH, OH or NH or derivatives thereof comprising reacting the ketone dimer of claim 5 with $NH_2$—O—$R_1$, (where $R_1$ is the appropriate substituent) under basic conditions followed by purification of the reaction mixture to separate the purified oxime.

9. The method of claim 5 where R5 is

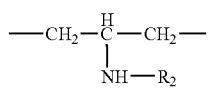

residue and $R_2$ is selected from H, or alkyl, cycloalkyl or aryl groups free or containing one of a variety of functional groups such as COOH, OH or NH or derivatives thereof comprising reacting the ketone dimer of claim 5 with $NH_2$—$R_2$ (where $R_2$ is the appropriate substituent) and sodium cyanoborohydride or sodium triacetoxyborohydride, followed by purification of the reaction mixture to separate the purified amine.

10. A compound of claim 3 where R and $R_1$ are as depicted in structure 6.

11. A pharmaceutical composition comprising the compound of claim 10 and a pharmaceutically acceptable carrier and/or excipient.

12. A method of treating Cancer or inhibiting cancer metastasis comprising administering to a subject suffering from Cancer an effective dosage of a composition of claim 11.

13. A method of treating a protozoal infection comprising administering to a subject suffering from an infection with an effective dosage of a composition of claim 11.

14. A method of preparing a compound of claim 10 comprising reaction of the ketone dimer 4 with aminoxy-acetic acid in the presence of sodium acetate followed by workup and purification of the reaction mixture.

15. A compound of claim 3 where R and $R_1$ are as depicted in structure 7.

16. A pharmaceutical composition comprising the compound of claim 15 and a pharmaceutically acceptable carrier and/or excipient.

17. A method of treating Cancer or inhibiting cancer metastasis comprising administering to a subject suffering from Cancer an effective dosage of a composition of claim 16.

18. A method of treating a protozoal infection comprising administering to a subject suffering from an infection with an effective dosage of a composition of claim 16.

19. A method of preparing a compound of claim 15 comprising reaction of the ketone dimer 4 with hydroxylamine hydrochloride in the presence of sodium acetate followed by workup and purification of the reaction mixture.

20. A compound of claim 3 where R and $R_1$ are as depicted in structure 8.

21. A pharmaceutical composition comprising the compound of claim 20 and a pharmaceutically acceptable carrier and/or excipient.

22. A method of treating Cancer or inhibiting cancer metastasis comprising administering to a subject suffering from Cancer an effective dosage of a composition of claim 21.

23. A method of treating a protozoal infection comprising administering to a subject suffering from an infection with an effective dosage of a composition of claim 21.

24. A method of preparing a compound of claim 20 comprising reaction of the ketone dimer 4 with O-benzyl hydroxylamine hydrochloride in the presence of sodium acetate followed by workup and purification of the reaction mixture.

25. A compound of claim 3 where R and $R_1$ are as depicted in structure 9.

26. A pharmaceutical composition comprising the compound of claim 25 and a pharmaceutically acceptable carrier and/or excipient.

27. A method of treating Cancer or inhibiting cancer metastasis comprising administering to a subject suffering from Cancer an effective dosage of a composition of claim 26.

28. A method of treating a protozoal infection comprising administering to a subject suffering from an infection with an effective dosage of a composition of claim 26.

29. A method of preparing a compound of claim 25 comprising reaction of the ketone dimer 4 with O-ethyl hydroxylamine hydrochloride in the presence of sodium acetate followed by workup and purification of the reaction mixture.

30. A compound as depicted in structure 10.

31. A pharmaceutical composition comprising the compound of claim 30 and a pharmaceutically acceptable carrier and/or excipient.

32. A method of treating Cancer or inhibiting cancer metastasis comprising administering to a subject suffering from Cancer an effective dosage of a composition of claim 31.

33. A method of treating a protozoal infection comprising administering to a subject suffering from an infection with an effective dosage of a composition of claim 31.

34. A method of preparing a compound of claim 30 comprising reaction of the glycerol dimer 5 with chlorosulphonic acid in the presence of pyridine followed by workup and purification of the reaction mixture.

35. A compound of claim 3 where R and $R_1$ are as depicted in structure 11.

36. A pharmaceutical composition comprising the compound of claim 35 and a pharmaceutically acceptable carrier and/or excipient.

37. A method of treating Cancer or inhibiting cancer metastasis comprising administering to a subject suffering from Cancer an effective dosage of a composition of claim 36.

38. A method of treating a protozoal infection comprising administering to a subject suffering from an infection with an effective dosage of a composition of claim 36.

39. A method of preparing a compound of claim 35 comprising reaction of the glycerol dimer 5 with 4-phenyl chloroformate and then adding 4-amino butyric acid allyl ester followed by deprotection of the resulting carbamate, workup and purification of the reaction mixture.

40. A compound of claim 3 where R and $R_1$ are as depicted in structure 12.

41. A pharmaceutical composition comprising the compound of claim 40 and a pharmaceutically acceptable carrier and/or excipient.

42. A method of treating Cancer or inhibiting cancer metastasis comprising administering to a subject suffering from Cancer an effective dosage of a composition of claim 41.

43. A method of treating a protozoal infection comprising administering to a subject suffering from an infection with an effective dosage of a composition of claim 41.

44. A method of preparing a compound of claim 40 comprising reaction of the ketone dimer 4 with benzyl amine, sodium triacetoxy borohydride and acetic acid followed by, workup and purification of the reaction mixture.

45. A compound of claim 3 where R and $R_1$ are as depicted in structure 13.

46. A pharmaceutical composition comprising the compound of claim 45 and a pharmaceutically acceptable carrier and/or excipient.

47. A method of treating Cancer or inhibiting cancer metastasis comprising administering to a subject suffering from Cancer an effective dosage of a composition of claim 46.

48. A method of treating a protozoal infection comprising administering to a subject suffering from an infection with an effective dosage of a composition of claim 46.

49. A method of preparing a compound of claim 45 comprising reaction of the ketone dimer 4 with 6-amino hexanoic acid, sodium triacetoxy borohydride and acetic acid followed by workup and purification of the reaction mixture.

* * * * *